US00PP34616P2

(12) United States Plant Patent
Elsworth

(10) Patent No.: US PP34,616 P2
(45) Date of Patent: Sep. 27, 2022

(54) ***AJUGA* PLANT NAMED 'TROTOU'**

(50) Latin Name: *Ajuga reptans*
Varietal Denomination: 'Trotou'

(71) Applicant: Kelly Elsworth, Portage, MI (US)

(72) Inventor: Kelly Elsworth, Portage, MI (US)

(73) Assignee: Christopher M. Hansen, Zeeland, MI (US)

( * ) Notice: Subject to any disclaimer, the term of this patent is extended or adjusted under 35 U.S.C. 154(b) by 0 days.

(21) Appl. No.: 17/687,440

(22) Filed: Mar. 4, 2022

(30) Foreign Application Priority Data

Dec. 23, 2021 (QZ) ..... 20213448

(51) Int. Cl.
*A01H 5/02* (2018.01)
*A01H 6/50* (2018.01)

(52) U.S. Cl.
USPC ..... Plt./401

(58) Field of Classification Search
USPC ..... Plt./401
See application file for complete search history.

*Primary Examiner* — Susan McCormick Ewoldt
(74) *Attorney, Agent, or Firm* — Penny J. Aguirre

(57) ABSTRACT

A new cultivar of *Ajuga* plant named 'Trotou' that is characterized by its foliage that is vibrant gold color with central mid-veins that are bright pink in color, its young stolon stems that are pink in color, its peduncle leaves that are purple in color at the tip of the flowering stems, and its high resistance to sun scorch and thrives in full sun in the summer in Michigan.

2 Drawing Sheets

Botanical classification: *Ajuga reptans.*
Variety denomination: 'Trotou'.

CROSS-REFERENCE TO RELATED APPLICATIONS

This application claims priority to European Community Plant Variety Office (CPVO) Plant Breeder's Rights Application No. 2021/3448 filed on Dec. 23, 2021, under 35 U.S.C. 119(f), the entire contents of which is incorporated by reference herein. This application is also co-pending with U.S. Plant Patent Applications filed for plants derived from the same breeding program that are entitled *Ajuga* Plant Named 'Fiefal' (U.S. Plant patent application Ser. No. 17/687,308) and *Ajuga* Plant Named 'Parpar' (U.S. Plant patent application Ser. No. 17/687,371).

BACKGROUND OF THE INVENTION

The present invention relates to a new and distinct cultivar of *Ajuga reptans* and will be referred to hereafter by its cultivar name, 'Trotou'. 'Trotou' represents a new cultivar of *Ajuga*, an herbaceous perennial grown for landscape use.

The new Invention arose from an ongoing controlled breeding program in Hudsonville, Mich. The objective of the breeding program is to develop new cultivars of *Ajugas* with unique foliage coloration, different leaf sizes and strong clump forming growth habits.

The new cultivar arose from a controlled cross made by the Inventor in March of 2019 between an unnamed and unpatented plant of *Ajuga reptans* with gold foliage as the female parent and 'Black Scallop' (U.S. Plant Pat. No. 15,815). The Inventor selected 'Trotou' as a single unique plant from amongst the seedlings of the above cross in May of 2020.

Asexual propagation of the new cultivar was first accomplished by stem tip cuttings in June of 2020 in Hudsonville, Mich. Propagation by stem tip cuttings and division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Trotou' as a unique cultivar of *Ajuga*.

1. 'Trotou' exhibits foliage that is vibrant gold color with central mid-veins that are pink in color.
2. 'Trotou' exhibits young stolon stems that are pink in color.
3. 'Trotou' exhibits peduncle leaves that are purple in color at the tip of the flowering stems.
4. 'Trotou' exhibits a high resistance to sun scorch and thrives in full sun in the summer in Michigan.

The female parent plant of 'Trotou' differs from 'Trotou' in having flowers that are pink color, young stolen stems and central mid-veins that are lime green in color, and terminal peduncle leaves that are light pink in color. The male parent plant of 'Trotou' differs from 'Trotou' in having foliage that is purple in color and young stolen stem growth that is purple-green in color. 'Trotou' can be most closely compared to *Ajuga reptans* cultivars 'Gold Chang' (U.S. Plant Pat. No. 32,751), 'Mahogany' (not patented), 'Fiefal' and 'Parpar'. 'Gold Chang' is similar to 'Trotou' in having foliage that is gold in color and in being a groundcover. 'Gold Chang' differs from 'Trotou' in having flowers that are light pink in color, stolon stems that are lime green in color, and in being highly susceptible to sun scorch. 'Mahogany' is similar to 'Trotou' in having flowers that are blue in color and in being a groundcover. 'Mahogany' differs from 'Trotou' in having foliage that is purple in color and stolon stems that are dark green in color. 'FieFal' differs from 'Trotou' in having black-purple foliage. 'Parpar' differs from 'Trotou' in having foliage that emerges dark burgundy in color and matures to yellow-green with apricot-burgundy colors as they mature and winter foliage that is red in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but are not limited to website publications by Romence Gardens, Plant Delights, Garden Solutions Plants, Great Garden Plants, In The Country Garden and Gifts, Wilson Bros Garden, White House Perennials, Mast Young Plants, Garden Crossings, Mountain Crest Gardens, Plant Central, Bloomin Designs, Chicago Botanic, Peace Tree Farm, Shop Bedners, Quality Cuttings, Bates Nursery, Pinterest, and Phoenix Perennials.

BRIEF DESCRIPTION OF THE DRAWINGS

The accompanying color photographs illustrate the overall appearance and distinct characteristics of 2-year-old plants of the new *Ajuga* as grown in a greenhouse in 1-gallon containers in Hudsonville, Mich.

The photograph in FIG. 1 provides a top view of 'Trotou'.

Figure 1:
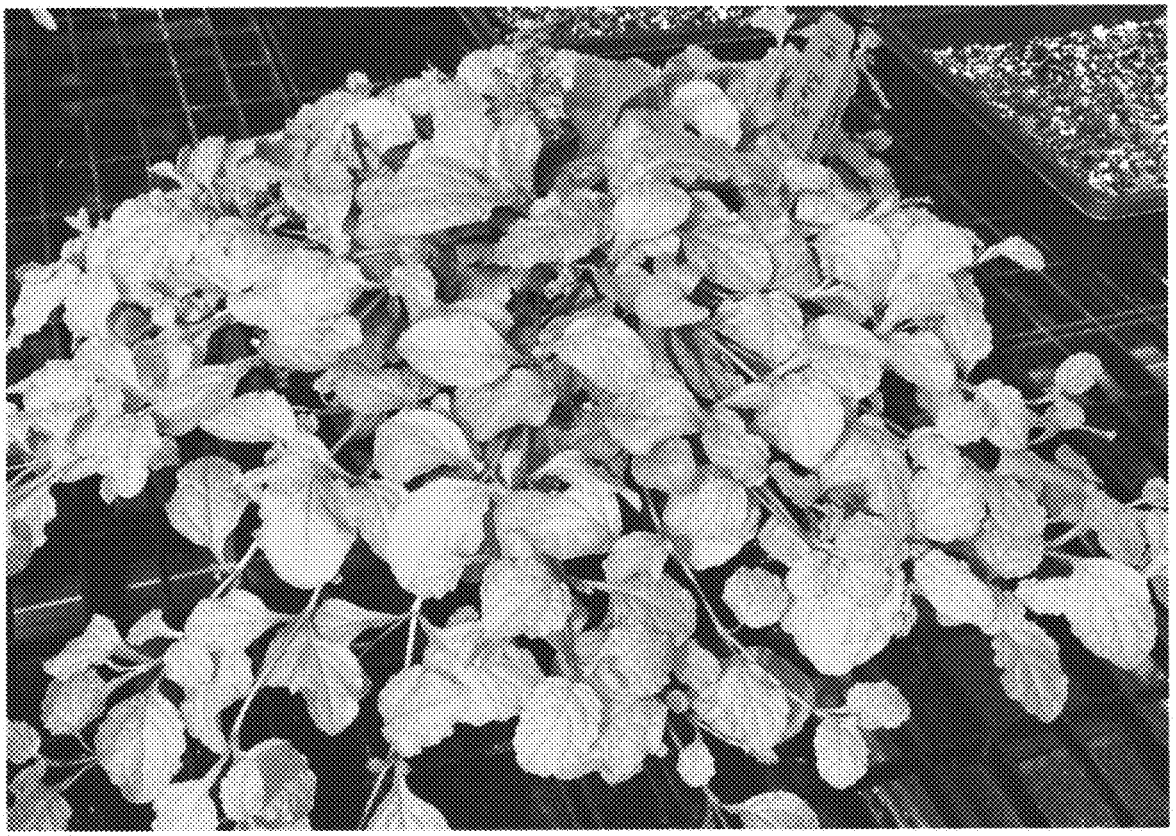
Figure 2:
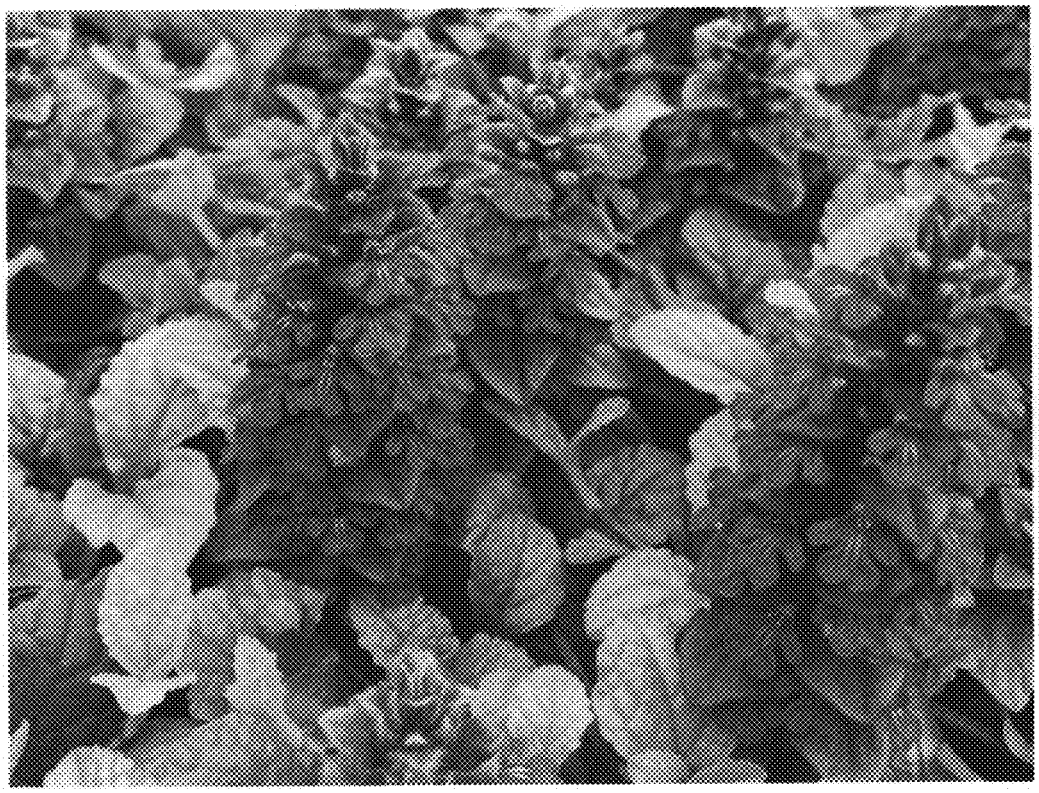

The photograph in FIG. 2 provides a close-up view of the inflorescences of 'Trotou'.

Figure 3:
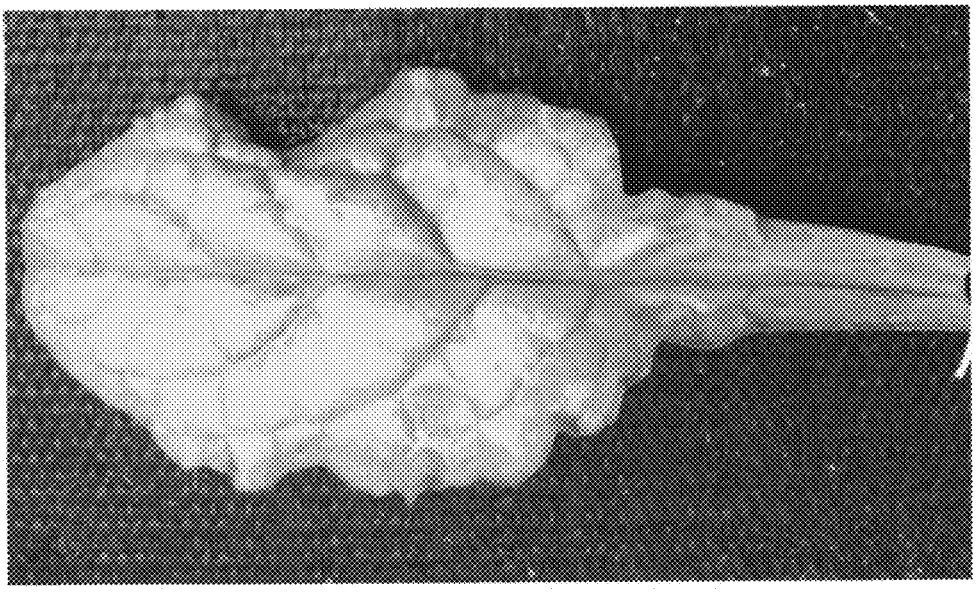

The photograph in FIG. 3 provides a close-up view of a leaf of 'Trotou'.

The colors in the photographs may differ slightly from the color values cited in the detailed botanical description, which accurately describe the colors of the new *Ajuga*.

DETAILED BOTANICAL DESCRIPTION

The following is a detailed description of 6-month-old plants of the new *Ajuga* as grown in 4-inch containers in a greenhouse in Hudsonville, Mich. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—4 to 6 weeks in late spring into summer in Michigan.

*Plant type.*—Herbaceous perennial.

*Plant habit.*—Dense, groundcover, compact upright inflorescences.

*Height and spread.*—15 cm in height (soil level to top of floral plane), an average of 11 cm in height (soil level to top of foliar plane) and 12 cm in width, mature plant in the landscape reaches an average of 10 cm in height and 46 cm in spread.

*Hardiness.*—At least in U.S.D.A. Zones 4 to 8.

*Diseases and pests.*—Plants have been observed to be disease free, however no resistance to any specific diseases is known, no resistance or susceptibility to pests has been observed.

*Root description.*—Fine and fibrous, a blend of 158A and NN155A in color.

*Propagation type.*—Tip stem cuttings and division.

*Root development.*—An unrooted stem cutting will fully root in a 50-cell plug in 8 weeks and a 50-cell plug will fully root in a 1-gallon container in 10 weeks.

*Growth rate.*—Highly vigorous.

*Branching habit.*—Basal rosettes of leaves from rhizomes.

*Stolon.*—Primarily 186B in color, an average of 3.5 mm in width, indeterminate length.

Foliage description:

*Leaf shape.*—Spatulate.

*Leaf division.*—Simple.

*Leaf base.*—Truncate to base of rhizome.

*Leaf apex.*—Broadly acute.

*Leaf venation.*—Pinnate, matches surface colors with upper surface main vein 158B flushed with 186A towards the base.

*Leaf margins.*—Undulate.

*Leaf attachment and arrangement.*—Whorled, held in in clumps.

*Leaf orientation.*—Upright and slightly outward.

*Leaf surface.*—Rugose, very finely puberulent on upper surface, slightly rough to the touch, glossy, lower surface glabrous and glossy.

*Leaf color.*—Young and mature upper surface; 154A, young and mature lower surface; 145A, peduncle leaves at the tip of the inflorescence are a blend of N77A and N77C, winter; 199D in color on both surfaces.

*Leaf size.*—Average of 11 cm in length and 3.5 cm in width.

*Leaf quantity.*—Average of 10 per 4-inch container.

*Leaf attachment.*—Sessile.

Flower description:

*Inflorescence type.*—Verticillaster, terminal spike, individual flowers in clusters held in leaf-axils.

*Inflorescence size.*—An average of 9 cm in height and 4 cm in width.

*Inflorescence number.*—50 to 70 blooms as a fully mature plant grown in a 1-gallon container.

*Lastingness of inflorescence.*—10 to 14 days, self-cleaning.

*Flower type.*—Labiate.

*Flower number.*—Average of 15 per inflorescence.

*Flower fragrance.*—None.

*Flower buds.*—Oblanceolate in shape, average of 3 mm in length and 2 mm in diameter, a blend of 92A and 92B in color, immature calyx 144A in color, surface matte and densely covered with long, soft woolly pubescence up to 3 mm in length with color matching surface colors.

*Flower size.*—Average of 1 cm in depth, 1 cm in diameter, throat 2 mm in diameter, tube 6 mm in length and 2 mm in diameter.

*Peduncles.*—An average of 10 cm in length, 5 mm in diameter, vertical angle, moderately strong, color; 185C, surface is very densely covered with long woolly hairs; up to 2 mm in length, translucent and matching surface color.

*Calyx.*—Rotate and tubular in shape, 3 mm in diameter.

*Sepals.*—5, 55% fused at base, average of 3 mm in length, 1 mm in width, ovate in shape, apex acute, entire margins, surface is heavily covered with long woolly hairs NN155D in color and translucent, surface color; inner and outer surface 144B.

*Petals.*—40% of petals fused into tube, upper central lobe; notched, average of 5 mm in length, 4 mm in width, rounded in shape, obtuse apex, entire margins, slightly recurved, upper and lower surface glabrous, satiny, color; upper surface when opening and fully open 97A, veins 83A, lower surface when opening and fully open 91C, outer lobes; 2, average of 3 mm in length, 2 mm in width, oblanceolate in shape, apex is obtuse, entire margins, no undulation, upper and lower surface glabrous and velvety, color; N89C, edges N89A, lower surface when opening and fully open 92A and 92B, flower throat and tube; outer and inner surface covered with woolly soft pubescence NN155D in color.

Reproductive organs:

*Pistils.*—1, style; 5 mm in length, color; 93B, top 92C, stigma; non-distinguishable, ovary; oblong, 1 mm in length and width, N144B in color.

*Stamens.*—4, filament; mostly implanted into flower tube, average of 2 mm in length, top 92D, anthers; club-shaped, 0.5 mm in diameter, 203A in color, pollen; moderate in quantity, 16A in color.

*Fruit.*—Fruit and seed production has not been observed to date.

It is claimed:

1. A new and distinct variety of *Ajuga* plant named 'Trotou' as described and illustrated herein.

* * * * *